(12) United States Patent
Svanerudh

(10) Patent No.: US 7,450,989 B2
(45) Date of Patent: Nov. 11, 2008

(54) METHOD AND DEVICE IN CONNECTION WITH PRESSURE MEASUREMENT

(75) Inventor: Johan Svanerudh, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 388 days.

(21) Appl. No.: 10/551,400

(22) PCT Filed: Mar. 3, 2004

(86) PCT No.: PCT/SE2004/000289

§ 371 (c)(1), (2), (4) Date: Oct. 31, 2005

(87) PCT Pub. No.: WO2004/087238

PCT Pub. Date: Oct. 14, 2004

(65) Prior Publication Data

US 2006/0212082 A1    Sep. 21, 2006

Related U.S. Application Data

(60) Provisional application No. 60/458,394, filed on Mar. 31, 2003.

(30) Foreign Application Priority Data

Mar. 31, 2003    (SE) .................................... 0300919

(51) Int. Cl.
    *A61N 1/00*    (2006.01)
(52) U.S. Cl. ..................................... 607/23
(58) Field of Classification Search ................ 607/17, 607/23; 600/485
    See application file for complete search history.

(56) References Cited

U.S. PATENT DOCUMENTS

| | | | |
|---|---|---|---|
| 4,562,843 A * | 1/1986 | Djordjevich et al. | ........ 600/485 |
| 5,129,394 A | 7/1992 | Mehra | |
| 5,226,423 A | 7/1993 | Tenerz et al. | |
| 5,626,623 A | 5/1997 | Kieval et al. | |
| 6,238,420 B1 | 5/2001 | Bakels et al. | |
| 6,463,324 B1 | 10/2002 | Ben-Haim et al. | |
| 7,110,817 B2 * | 9/2006 | Yu et al. | ........................ 607/23 |
| 2002/0072880 A1 | 6/2002 | Svanerudh et al. | |
| 2002/0133198 A1 | 9/2002 | Kramer et al. | |

* cited by examiner

*Primary Examiner*—George Manuel
(74) *Attorney, Agent, or Firm*—Foley & Lardner LLP

(57) ABSTRACT

Pressure measurement device (2) including a pressure sensor (6) adapted to perform pressure measurements in the left ventricle of a heart (8). The sensor is connected to a measurement unit (10) to receive pressure measurement values obtained from the sensor, and to a processing means (12) for determining a set of pressure values, said processing means then determines a set of first order time derivative values determined from the set of pressure values. The said processing means also calculates a value of a prefined parameter of the set of first order time derivative values during said measurement period, the predefined parameter is the average or median value of the maximum value of the set of first order time derivative values, wherein the pressure measurements are performed during measurement periods using predetermined medical implant settings in a medical implant (20) controlling the application of stimulation pulses at least in the left and right ventricles of the heart, and that the implant setting include a first time difference 1 being the time between stimulations in the left and right ventricles.

21 Claims, 4 Drawing Sheets

METHOD AND DEVICE IN CONNECTION WITH PRESSURE MEASUREMENT

FIELD OF THE INVENTION

The present invention relates to a device and a method for measuring blood pressure.

BACKGROUND OF THE INVENTION

A biventricular pacing system includes pacing electrodes arranged at least in both the left and right ventricles of the heart. This type of systems also often includes an atrial electrode arranged in the right atrium.

The present invention is applicable both during procedures of implanting electrode leads connected to medical implants, e.g. pacemakers, defibrillators or cardioverters, and at later follow-up procedures for evaluating the positions of the electrodes in the heart. In order to achieve a desired effect of a stimulation pulse it is of great importance that the electrode surface has good contact with the heart tissue so that the tissue may be stimulated by using stimulation pulses having as low stimulation energy as possible. In biventricular systems the timing or synchronization between stimulation pulses applied to the right and left ventricle is very important in order to adapt the stimulation as much as possible to the heart's intrinsic rhythm. The synchronization is related to the cardiac output and a general object for pacemakers is to achieve as high cardiac output as possible.

In U.S. Pat. No. 6,238,420 is known a four-chamber pacing system for optimizing cardiac output and determining heart conditions. The system utilizes impedance sensing for determining optimum pacing parameters, e.g., for pacing the left ventricle so that left heart output is maximized. Impedance sensing in the left heart also provides timing of mechanical contraction, and the pacemaker controls pacing to maintain bi-ventricular mechanical synchronization adjusted for maximum cardiac output.

In connection with implantable heart stimulators it has been found very advantageous to measure the pressure in the left ventricle of the heart in order to obtain information related to the function of the heart stimulator and especially if the desired therapy is achieved by the stimulating pulses.

A pressure sensor assembly mounted on a guide wire and applicable for measuring intravascular pressure, and in particular intracardiac pressure, is disclosed in U.S. Pat. No. 5,226,423. The pressure sensor assembly is in particular applicable for insertion into the left ventricle of the heart via coronary sinus, according to well-established implantation techniques.

In the published US patent application 2002/0072880 is disclosed a system that includes an interactive graphical user interface for controlling the performance of, and for displaying on a screen, measured values and calculated results based on the measured values obtained by a guidewire-mounted pressure sensor, e.g of the kind disclosed in the above-mentioned U.S. Pat. No. 5,226,423.

The overall object with the present invention is to simplify for the physician, during the clinical procedure of implantation or follow-up, to use information obtained by pressure measurements in the left ventricle to optimize predetermined medical implant settings in a medical implant controlling the application of stimulation pulses to the left and right ventricles of the heart.

SUMMARY OF THE INVENTION

Thus, for each stimulation setting the pressure value in the left ventricle is continuously measured and preferably displayed at a display means. The first order time derivative of the measured pressure value is simultaneously determined and preferably also displayed at the display means. The average or median value of the maximum values of the first order time derivative pressure values is determined for a present measurement period.

This is repeated for a number of different stimulation settings and the average/median value for each setting is displayed together with identification data. The identification data includes the stimulation setting (being the AV and VV intervals, where AV designates the time between applying stimulation pulses to the atrium and the ventricle of the heart and VV designates the time between applying stimulation pulses to the right and left ventricle of the heart). By using this information presented on an measurement session list the physician may easily identify the optimal setting, being the setting where the average value is maximal. Alternatively, the information may be presented directly in a two-, or three-dimensional graph.

The pressure is preferably measured by using a miniaturised pressure sensor arranged at the distal end of a pressure sensing guidewire inserted into the left ventricle according to well-established technique. The measured pressure and the calculated first derivate of the pressure is displayed in real-time on a display means and the average value of the maximum derivative is determined. A number of measurements are performed for different $V_{right}$-$V_{left}$ values where $V_{right}$ is the time when stimulating in the right ventricle and $V_{left}$ is the time when stimulating in the left ventricle. Thus, the time difference $\Delta$ is preferably in the range of $-100$-$100$ ms. The time difference is determined where the average value of the maximum derivative is maximal.

Also the AV interval, being the time between atrial and ventricular stimulation in the right side of the heart, may be varied (preferably between 30 and 120 ms) in order to obtain an optimal setting for the pacemaker.

Further calculations may be performed, e.g. second time derivative values of the pressure curve may be determined and used in the process.

According to an alternative embodiment of the present invention the pressure sensor is instead arranged at a heart electrode lead inserted into the left ventricle and the above-mentioned processing of the obtained pressure value is accomplished by an implanted heart stimulating device to which the electrode lead is connected.

SHORT DESCRIPTION OF THE APPENDED DRAWINGS

DETAILED DESCRIPTION OF PREFERRED EMBODIMENTS OF THE INVENTION

The present invention will now be described with references to the accompanying figures.

Figure 1:
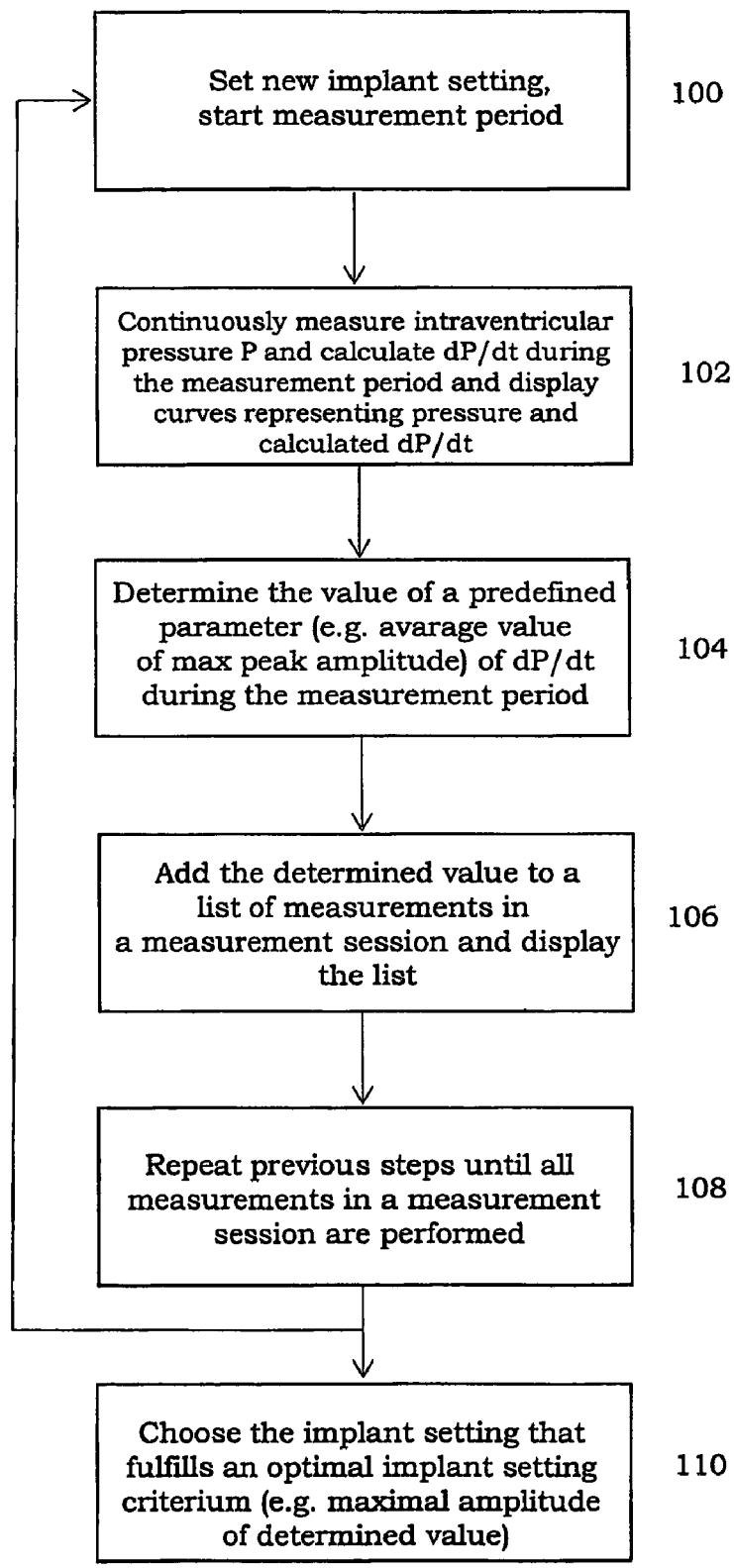
FIG. 1 shows a flowchart of the method according to the present invention.

In FIG. 1 a flowchart is illustrated of the method according to the invention.

A measurement session is initiated by determining an appropriate initial implant setting for the medical implant to be tested. The setting to be tested is inputted at a "View" display screen (see below in connection with the description of FIG. 5) and the medical implant (ref. sign 20 in FIG. 2) is programmed with that setting by the medical implant programmer (22 in FIG. 2) in accordance with well-known techniques. After that the measurement period may start. (step 100).

The implant setting includes a first time difference Δ1 being the time between stimulations in the left and right ventricles. If also an atrial electrode lead is implanted (see FIG. 3) the implant setting further includes a second time difference Δ2 being the time between stimulations in the right atrium and right ventricle, or alternatively the right atrium and the left ventricle.

In one straight-forward use of the present invention the implant setting is varied by the physician that manually inputs different values at the display screen and then manually programs the medical implant with that value(s). An obvious alternative would be to perform this "value search" automatically. This could be done either under control from the medical implant programmer or under control from the pressure measurement device. In both cases the implant device setting is varied according to a predefined search pattern where all possible, or a predetermined subset of all possible, combinations of AV- and VV-intervals are checked with regard to the measured pressure and calculated dP/dt. There are numerous different search methods that may be used in order to identify "the best" combination of values by using as few iterations as possible.

The inventive method for monitoring, determining by measurement and calculation and graphically displaying physiological variables related to blood pressure, comprises at least the following steps:

a) detecting continuously during a measurement period left ventricular pressure of a heart ($P_{LV}$), derived from a guidewire-mounted pressure sensor;
b) transducing said pressure to a processable signal and delivering said processable signal to a processing means being able to process said processable signal;
c) receiving said processable signal;
d) calculating the first order time derivative ($dP_{LV}/dt$) of said left ventricular pressure by processing said signal;
e) forming and displaying data representing the pressure ($P_{LV}$) values and the first order time derivative values of said pressure ($dP_{LV}/dt$). All these steps a)-e) are covered by step 102 in FIG. 1.

The method is continued by step 104:

f) calculating the value of a predefined parameter of said first order time derivative values during the measurement period, and step 106:
g) displaying said calculated value in a measurement session list that may include calculated values from other measurement periods.

The measurement session list will be further discussed below in relation to FIG. 5.

The predefined parameter is the average value, or alternatively the median value, of the peak values of the set of first order derivative values during a measurement period.

In situations where artefacts and disturbances are to be suppressed only part(s) of the first time derivative curve that fulfil certain calculation criteria are included when calculating the value of the predefined parameter. This criteria may include certain max and min limits for the peak values in order to include them in the average/median value calculation.

As initially stated the pressure measurement is performed during a measurement period using predetermined medical implant settings in a medical implant controlling the application of stimulation pulses at least to the left and right ventricles of the heart.

When the measurements are performed for all different settings the method according to a preferred embodiment further comprises the step of choosing the implant setting from the list that fulfils an optimal implant setting criterion. The optimal implant setting criterion is to choose the implant setting having the maximum amplitude of the average, or median, values in the list.

The abovementioned measurement period is less than 30 seconds and preferably about 10 seconds.

A measurement session list may include calculated values from measurement periods obtained during a measurement session of less than 60 minutes and preferably less than 30 minutes.

The present invention also relates to a computer program product directly loadable into the data storage (ref. sign 16 in FIG. 3) of the processing means within a control unit arranged in the pressure measurement device. The computer program product comprises the software code means for performing the steps of the disclosed method.

The invention further comprises a computer program product that can be stored on a computer usable medium, comprising readable program for causing a processing means in a control unit to control an execution of the steps of the disclosed method.

The invention further comprises a computer program product that can be stored on a computer usable medium, comprising readable program for causing a processing means in a control unit to control an execution of the steps of any of the appended method claims.

Figure 2:
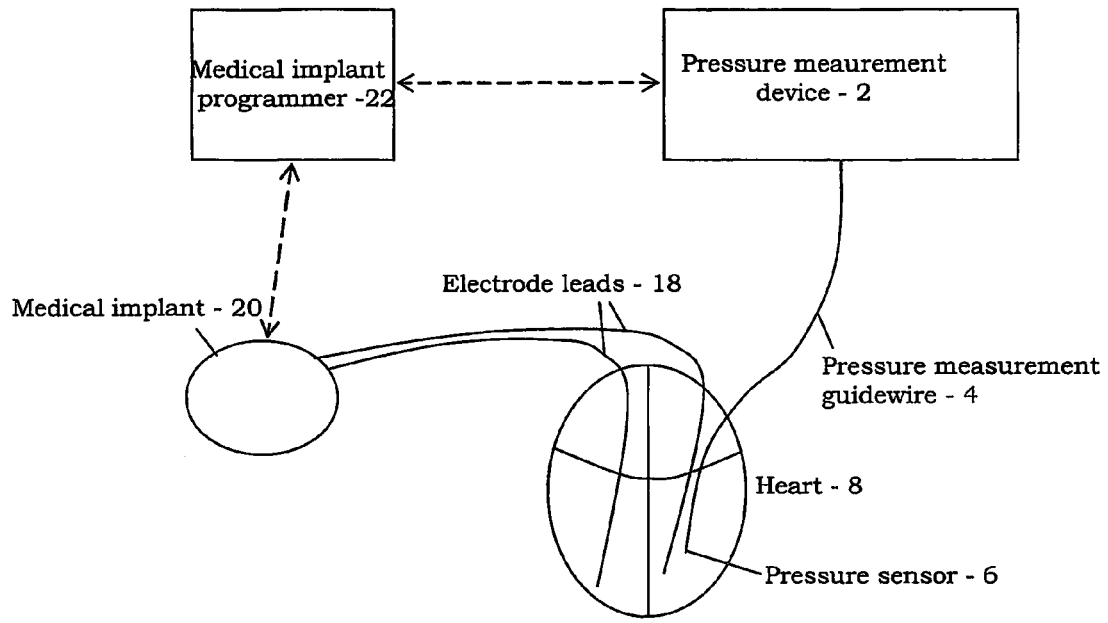
FIG. 2 is a block diagram including a pressure measurement device according to the present invention.
Figure 3:
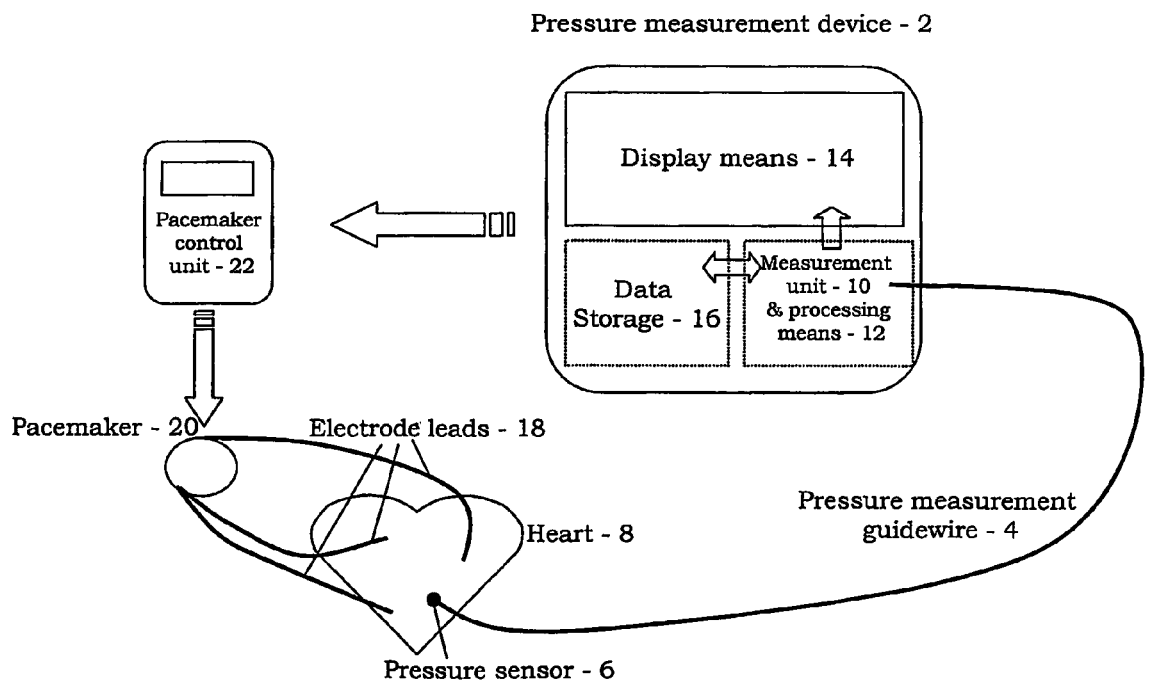
FIG. 3 is a block diagram including a pressure measurement device of a preferred embodiment according to the present invention.

With references to FIGS. 2 and 3 showing block diagrams of the present invention the pressure measurement device now will be further described.

The pressure measurement device 2 includes a pressure measurement guidewire 4 provided with a pressure sensor 6 adapted to perform pressure measurements in the left ventricle of a heart 8. The wire is connected to a measurement unit 10 to receive pressure measurement values obtained from the sensor, and to a processing means 12 for determining pressure values and the measurement device preferably also includes a display means 14 for displaying the pressure values during a measurement period. This may preferably be performed in real-time.

The processing means then determines a set of first order time derivative values determined from the pressure values and the display means 14 (if present) displays the determined first order time derivative values, and the processing means also calculates and displays a value of a predefined parameter of the first order time derivative values during said measurement period. The external parts of the pressure measurement device may be implemented as a special purpose device solely tailored for this use or in a general purpose device, e.g. a PC, a lap-top PC, or any computing device, provided with the necessary equipment for communicating with the rest of the device, e.g. the pressure sensor.

The pressure measurement device is adapted to implement the method described above in accordance with all details given in the description of the method.

The bi-directed arrow between the pressure measurement device 2 and the medical implant programmer 22 indicates the communication between these units. This could be either by manual programming of the programmer by the physician or automatically if an automatic value search is performed. The arrow between the medical implant and the programmer 22 indicates normal bi-directed telemetry communication.

In FIG. 3 a block diagram illustrates a preferred embodiment where further details of the measurement device 2 are illustrated. Herein the pacemaker 20 is provided with an atrial electrode lead in addition to the leads shown in FIG. 2. The arrows indicate one typical procedure when implementing the inventive method: the implant setting is inputted at the display screen of the display means 14; these setting are then communicated by the pacemaker control unit 22 to the pacemaker 20 that applies the setting. The pressure sensor measures the pressure during a measurement period in accordance with the method as previously described.

According to an alternative embodiment of the present invention the pressure sensor is instead arranged at a heart electrode lead inserted into the left ventricle and the above-mentioned processing of the obtained pressure value is accomplished by an implanted heart stimulating device to which the electrode lead is connected. In this embodiment the processing may be performed automatically in order to continuously optimize the implant settings. The values may be stored by the implant and transmitted out to the programmer to be displayed and further analysed.

Figure 4:
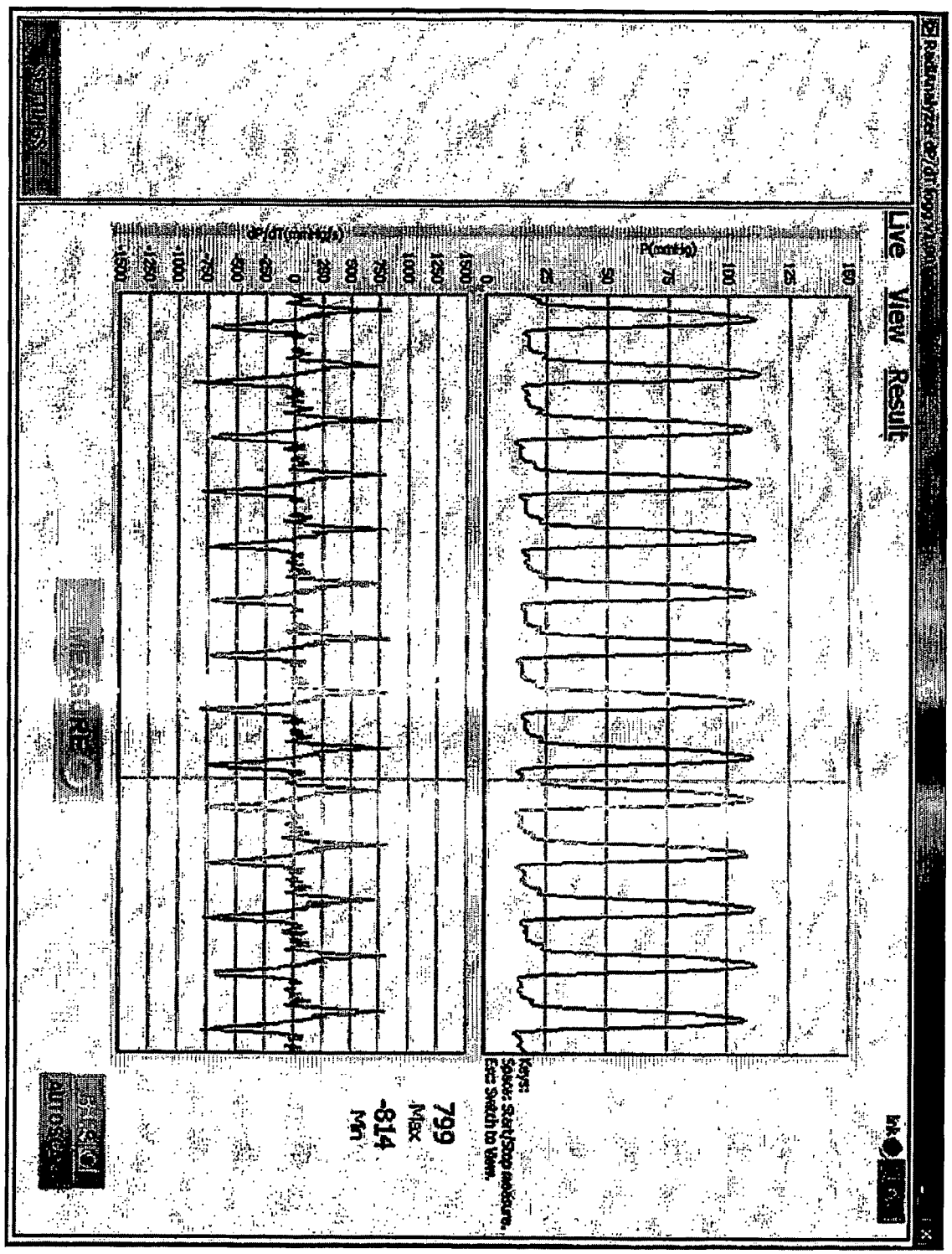
FIG. 4 shows an image of a first screen display illustrating the present invention.

FIG. 4 shows an image of a first screen display illustrating the present invention.

The pressure measurement device includes a display means being an interface for controlling the pressure measurements and for displaying curves and values. In FIG. 4 a first screen display is shown, being the "Live" display, which shows the curves of the pressure and the calculated derivative during the measurements. The vertical axes designate the pressure in mmHg and dP/dt in mmHg/s, respectively. The horizontal axes cover a measurement period of approximately 7 seconds. The measurement is initiated by pressing the measure button in the middle at the bottom of the screen and terminated by pressing a stop button (not shown). The figures to the right on the screen show the maximum and the minimum values of the first order time derivative values of the measurement period.

Figure 5:
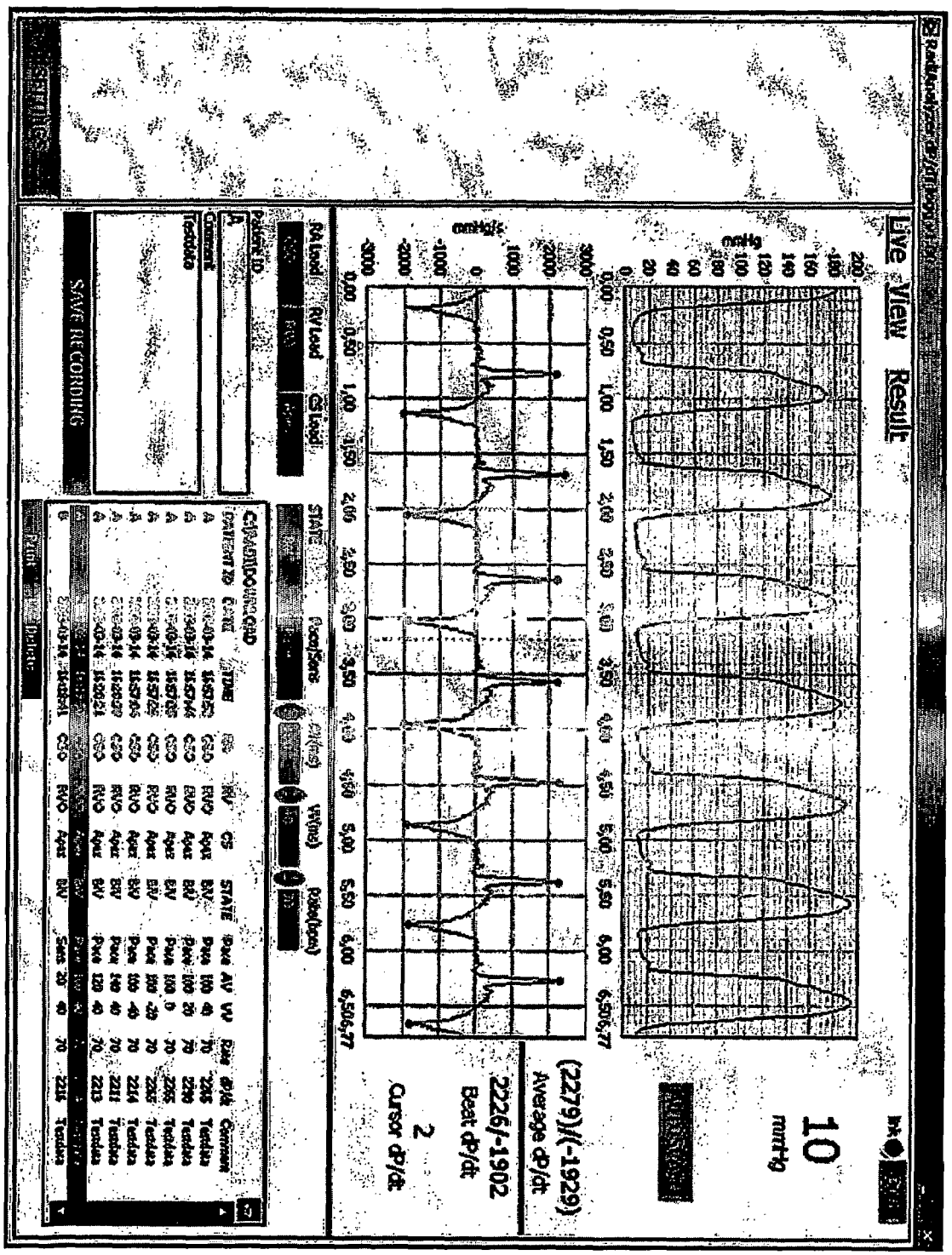
FIG. 5 shows an image of a second screen display illustrating the present invention.

When the measurement is performed the "View" button may be pressed and then the screen display as shown in FIG. 5 becomes visible.

The upper curve shows the pressure curve for the obtained pressure during the measurement period and the lower curve shows the first derivative curve of the pressure curve. These curves have the same designations of the axes as the curves in FIG. 4.

In the upper curve a vertical cursor line can be seen at approximately 3,10 seconds. This line may be moved by some kind of pointer means, e.g. a mouse, and in the upper right part of the display screen the pressure value at the location of the cursor line is indicated, in this case 10 mmHg.

In the lower curve, showing the derivative curve, the extreme points are indicated by white markings. A dashed cursor line can be seen at approximately 3,20 seconds and the dP/dt value is shown to the right, in this case 2.

Above this, the calculated average values for the maximum and minimum dP/dt are shown, in this case (2279)/(−1929).

Below that is shown the maximum and minimum values for the heart cycle where the cursor is located, in this case 2226/−1902.

The measurement session list is shown as a table at the bottom of the screen display. The table includes inter alia patient identity, date, time, type of electrodes (RA, RV, CS), state (here biventricular stimulation), AV-interval and VV-interval, Rate, calculated dP/Dt and also a comment field.

Above the table is shown a bar where values for some of these parameters may be inputted. These parameters are primarily related to the settings of the medical implant. In the bar from left to right: RA lead (right atrial lead) in position CSO (coronary sinus ostium); RV lead (right ventricular lead) in position RVO (right ventricular outflow); CS lead (coronary sinus lead) in position (superior-inferior position) Apex (apical position); STATE BiV (biventricular pacing); Pace/Sens (indicates if in pacing or sensing mode); AV(ms)—the value of the AV-interval presently used by the pacemaker; VV(ms)—the value of the VV-interval presently used by the pacemaker; Rate (bpm)—presently used stimulation rate.

It should be noted that it is not necessary to use all fields, e.g. if no atrial electrode is used there is no AV-interval available.

In a third display screen (not shown), which is available when pressing the "Result"-button, the table is graphically displayed. This may be in a two-dimensional curve having VV-values along the x-axis and dP/dt along the y-axis where the peak value of that curve indicates an optimal setting for the medical implant.

In an alternative display screen also the AV-values are used and plotted along the z-axis. The display screen then shows a three-dimensional illustration of the calculated result. The optimal setting may then be found where the 3D-curve has its maximum.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A pressure measurement device comprising:
a pressure sensor adapted to perform pressure measurements in a left ventricle of a heart, wherein the pressure sensor is connected to a measurement unit to receive pressure measurement values obtained from said sensor, and
a processing means adapted to determine, during a number of measurement periods, each measurement period including a number of heart cycles, a set of pressure values and a set of first order time derivative values determined from the set of pressure values,
wherein said processing means also is adapted to calculate maximum first order time derivative values for each of the heart cycles during one measurement period, and to calculate a predefined parameter,
wherein the predefined parameter is an average or median value of said maximum first order time derivative values from the one measurement period,
wherein the pressure measurements are adapted to be performed during measurement periods related to different predetermined medical implant settings in a medical implant controlling application of stimulation pulses at least in the left and right ventricles of the heart,
wherein the different predetermined medical implant settings include that of a VV-interval, and wherein an optimal medical implant device setting of the VV-interval is identified as a setting where the predefined parameter is maximal.

2. The pressure measurement device according to claim 1, further comprising a display means for displaying, during a measurement period, curves representing the set of pressure values and the determined first order time derivative values.

3. The pressure measurement device according to claim 1, further comprising a pressure measurement guidewire at which said pressure sensor is arranged.

4. The pressure measurement device according to claim 1, wherein the pressure measurement device is arranged in said medical implant, said medical implant being a heart stimulating device and wherein said pressure sensor is arranged at a heart electrode lead connected to said heart stimulating device.

5. The pressure measurement device according to claim 4, wherein the heart stimulating device is a pacemaker, cardioverter or defibrillator.

6. The pressure measurement device according to claim 1, wherein the calculated value of the predefined parameter is added to a measurement session list of measurement periods.

7. The pressure measurement device according to claim 1, wherein the pressure measurement is repeated for other predefined implant device settings.

8. The pressure measurement device according to claim 1, wherein implant device settings are adapted to be varied during a measurement session according to a predefined search pattern.

9. The pressure measurement device according to claim 2, wherein calculated values of the predefined parameter are displayed in a three dimensional illustration.

10. The pressure measurement device according to claim 1, wherein the different predetermined medical implant settings also include that of an AV-interval.

11. A method for monitoring, determining by measurement and calculation, and graphically displaying physiological variables related to blood pressure, comprising at least the following steps:
a) detecting continuously during at least one measurement period left ventricular pressure of a heart ($P_{LV}$), derived from a guidewire-mounted pressure sensor;
b) transducing said left ventricular pressure to a processable signal and delivering said processable signal to a processing means being able to process said processable signal;
c) receiving said processable signal;
d) calculating a first order time derivative ($dP_{LV}/dt$) of said left ventricular pressure by processing processable said signal;
e) forming and displaying a set of values representing the left ventricular pressure ($P_{LV}$) and a set of vaules representing the first order time derivative of said left ventricular pressure ($dP_{LV}/dt$);
f) calculating a value of a predefined parameter of said set of first order time derivative values during the at least one measurement period, wherein the predefined parameter is an average or median value of maximum values of the set of first order time derivative values for each heart cycle during the at least one measurement period, wherein the pressure measurements are performed during a plurality measurement periods using predetermined medical implant settings in a medical implant controlling application of stimulation pulses at least in left and right ventricles of the heart, wherein the predetermined medical implant settings include that of an VV-interval and a first time difference $\Delta 1$, wherein the first time difference is a time between stimulations in the left and right ventricles,
g) displaying said calculated value of the predefined parameter in a measurement session list that includes calculated values of the predefined parameter from other measurement periods, and
h) choosing a predetermined medical implant settings include that of an VV-interval from the measurement session list that fulfills an optimal implant setting criterion.

12. A method according to claim 11, wherein in step f) only parts of the set of first order time derivative values that fulfill certain calculation criteria are included in calculating the value of the predefined parameter such that artifacts and disturbances are suppressed.

13. A method according to claim 12, characterized in that said optimal implant setting criterion is to choose the maximum amplitude of the average values.

14. A method according to claim 11, wherein the predetermined medical implant settings further include a second time difference $\Delta 2$, the second time difference being a time between stimulations in a right atrium and the right or left ventricle.

15. A method according to claim 11, wherein implant device settings are is varied according to a predefined search pattern.

16. A method according to claim 11, wherein the at least one measurement period is less than 30 seconds.

17. A method according to claim 11, wherein a measurement session list includes calculated values of the predefined parameter from measurement periods obtained during a measurement session of less than 60 minutes.

18. The method according to claim 11, wherein the predetermined medical implant settings also include that of an AV-interval.

19. A computer program directly loadable into an internal memory storage of a processing means within a control unit, comprising software code means for performing the following steps:
a) detecting continuously during at least one measurement period left ventricular pressure of a heart ($P_{LV}$), derived from a guidewire-mounted pressure sensor;
b) transducing said left ventricular pressure to a processable signal and delivering said processable signal to a processing means being able to process said processable signal;
c) receiving said processable signal;
d) calculating a first order time derivative ($dP_{LV}/dt$) of said left ventricular pressure by processing processable said signal;
e) forming and displaying a set of values representing the left ventricular pressure ($P_{LV}$) and a set of vaules representing the first order time derivative of said left ventricular pressure ($dP_{LV}/dt$);
f) calculating a value of a predefined parameter of said set of first order time derivative values during the at least one measurement period, wherein the predefined parameter is an average or median value of maximum values of the set of first order time derivative values for each heart cycle during the at least one measurement period, wherein the pressure measurements are performed during a plurality measurement periods using predetermined medical implant settings in a medical implant controlling application of stimulation pulses at least in left and right ventricles of the heart, wherein the predetermined medical implant settings include that of an VV-interval and a first time difference Δ1, wherein the first time difference is a time between stimulations in the left and right ventricles, g) displaying said calculated value of the predefined parameter in a measurement session list that includes calculated values of the predefined parameter from other measurement periods, and h) choosing a predetermined medical implant settings include that of an VV-interval from the measurement session list that fulfills an optimal implant setting criterion.

20. A computer program that can be stored on a computer usable medium, comprising readable program code for causing a processing means in a control unit to control an execution of the following steps:

a) detecting continuously during at least one measurement period left ventricular pressure of a heart ($P_{LV}$), derived from a guidewire-mounted pressure sensor;

b) transducing said left ventricular pressure to a processable signal and delivering said processable signal to a processing means being able to process said processable signal;

c) receiving said processable signal;

d) calculating a first order time derivative ($dP_{LV}/dt$) of said left ventricular pressure by processing processable said signal;

e) forming and displaying a set of values representing the left ventricular pressure ($P_{LV}$) and a set of vaules representing the first order time derivative of said left ventricular pressure ($dP_{LV}/dt$);

f) calculating a value of a predefined parameter of said set of first order time derivative values during the at least one measurement period, wherein the predefined parameter is an average or median value of maximum values of the set of first order time derivative values for each heart cycle during the at least one measurement period, wherein the pressure measurements are performed during a plurality measurement periods using predetermined medical implant settings in a medical implant controlling application of stimulation pulses at least in left and right ventricles of the heart, wherein the predetermined medical implant settings include that of an VV-interval and a first time difference Δ1, wherein the first time difference is a time between stimulations in the left and right ventricles, g) displaying said calculated value of the predefined parameter in a measurement session list that includes calculated values of the predefined parameter from other measurement periods, and h) choosing a predetermined medical implant settings include that of an VV-interval from the measurement session list that fulfills an optimal implant setting criterion.

21. A pressure measurement device comprising:

a pressure sensor adapted to perform pressure measurements in a left ventricle of a heart, wherein the pressure sensor is connected to a measurement unit to receive pressure measurement values obtained from said sensor, and a processor adapted to determine, during a number of measurement periods, each measurement period including a number of heart cycles, a set of pressure values and a set of first order time derivative values determined from the set of pressure values, wherein said processor also is adapted to calculate maximum first order time derivative values for each of the heart cycles during one measurement period, and to calculate a predefined parameter, wherein the predefined parameter is an average or median value of said maximum first order time derivative values from the one measurement period, wherein the pressure measurements are adapted to be performed during measurement periods related to different predetermined medical implant settings in a medical implant controlling application of stimulation pulses at least in the left and right ventricles of the heart, wherein the different predetermined medical implant settings include that of a VV-interval, and wherein an optimal medical implant device setting of the VV-interval is identified as a setting where the predefined parameter is maximal.

\* \* \* \* \*